United States Patent
Marmur et al.

(10) Patent No.: US 10,383,809 B2
(45) Date of Patent: Aug. 20, 2019

(54) SKIN TREATMENT COMPOSITIONS, MASKS AND RELATED METHODS

(71) Applicant: Galactic Beauty, LLC, New York, NY (US)

(72) Inventors: Ellen Marmur, New York, NY (US); Alison Cutlan, Brooklyn, NY (US)

( * ) Notice: Subject to any disclaimer, the term of this patent is extended or adjusted under 35 U.S.C. 154(b) by 363 days.

(21) Appl. No.: 15/405,621

(22) Filed: Jan. 13, 2017

(65) Prior Publication Data

US 2018/0200174 A1    Jul. 19, 2018

(51) Int. Cl.

| | |
|---|---|
| *A61K 36/00* | (2006.01) |
| *A61K 8/66* | (2006.01) |
| *A61K 8/02* | (2006.01) |
| *A61K 8/97* | (2017.01) |
| *A61K 8/99* | (2017.01) |
| *A61N 5/06* | (2006.01) |
| *A61Q 19/08* | (2006.01) |
| *A61Q 19/00* | (2006.01) |
| *A61K 8/04* | (2006.01) |
| *A61K 8/9706* | (2017.01) |
| *A61K 8/9789* | (2017.01) |

(52) U.S. Cl.
CPC .............. *A61K 8/66* (2013.01); *A61K 8/0212* (2013.01); *A61K 8/0216* (2013.01); *A61K 8/042* (2013.01); *A61K 8/97* (2013.01); *A61K 8/9706* (2017.08); *A61K 8/9789* (2017.08); *A61K 8/99* (2013.01); *A61N 5/062* (2013.01); *A61N 5/0616* (2013.01); *A61Q 19/00* (2013.01); *A61Q 19/08* (2013.01); *A61K 2800/81* (2013.01); *A61N 2005/0663* (2013.01)

(58) Field of Classification Search
CPC ............................. A61K 36/00; A61K 35/741
See application file for complete search history.

(56) References Cited

U.S. PATENT DOCUMENTS

| | | | | |
|---|---|---|---|---|
| 2004/0219124 | A1* | 11/2004 | Gupta | A61K 8/0212 424/70.13 |
| 2008/0206211 | A1* | 8/2008 | Gueniche | A61K 8/981 424/93.42 |

OTHER PUBLICATIONS

PhytoRNx, trademark registration, bibliographic information, 2016.*

\* cited by examiner

*Primary Examiner* — Rosanne Kosson
(74) *Attorney, Agent, or Firm* — Cozen O'Connor

(57) ABSTRACT

The present disclosure describes a topical composition, and related masks comprising the compositions disclosed herein, for applying to skin for treating acne or skin rejuvenation, the compositions comprising a light activated enzymatic extract; adaptogenic Baobab (*Adansonia digitata*) seed extract; adaptogenic wild indigo (*Tephrosia purpurea*) extract; pre- and/or pro-biotic extracts; and a carrier. The mask may be embodied in, or comprise, a hydrogel matrix or a biocellulose material or other fibrous material.

15 Claims, No Drawings

SKIN TREATMENT COMPOSITIONS, MASKS AND RELATED METHODS

BACKGROUND

Natural products are essential sources of cosmetics and medicines. The World Health Organization estimates that 80% of the world's population relies on traditional medicines made from natural products. The modern pharmaceutical industry is also dependent on plant-based medicines, with as much as 50% of all drugs based on or derived from natural products. As such, plants and other natural products offer excellent sources of health-promoting cosmetics and medicines.

BRIEF SUMMARY

The present disclosure is directed to compositions, devices and related methods for treatment of skin. The compositions, devices and related methods of the present disclosure also provide maintenance treatment, acne treatment, rejuvenation treatment, and anti-aging treatment for skin.

In one aspect, the present disclosure provides topical compositions for applying to skin comprising a light activated enzymatic extract; Baobab (*Adansonia digitata*) seed extract; wild indigo (*Tephrosia purpurea*) extract; pre- and/or pro-biotic extracts; and a carrier. The compositions may be in a topical gel form.

In some embodiments, the light activated enzymatic extract comprises an enzyme from a blue-green algae (e.g., *Anacystis nidulans*), such as, for example, photolyase. The light activated enzymatic extract may comprise components selected from the group consisting of photolyase, planktonic enzymes, acai polyphenols, tara tree extract, seaweed extract, and/or combinations thereof.

In some embodiments, the light activated enzymatic extract is activated by light of wavelength from about 420 nm to about 460 nm. In other embodiments, the light activated enzymatic extract is activated by light of wavelength from about 630n to about 700 nm.

In some embodiments, the Baobab seed extract comprises plant ribonucleic acid molecules.

In some embodiments, the wild indigo extract is from the seed of the plant.

In some embodiments, the compositions may further include one or more of the following: willowherb extract, colloidal sulfur, niacinamide, a *Thermus thermophilus* extract, narnginen, provitamin B5, *arnica* extract, one or more growth factors, night blooming Chinese cucumber extract, night blooming *cereus* cactus, chamomile, lavender, and night blooming jasmine.

In another aspect, the present disclosure provides topical compositions for applying to skin comprising a heat activated enzymatic extract, such as, e.g., *Thermus thermophiles* extract; Baobab (*Adansonia digitata*) seed extract; wild indigo (*Tephrosia purpurea*) extract; pre- and/or pro-biotic extracts; and a carrier. These compositions may also be in a topical gel form. These compositions may also comprise light activated enzymatic extracts, as described herein.

In another aspect, the present disclosure provides cosmetic masks for application to skin, the masks comprising a hydrogel or cotton fiber or bio-cellulose matrix comprising the topical composition of the present disclosure embedded therein.

In another aspect, the present disclosure provides methods of treating skin for acne or skin rejuvenation, the methods comprising placing the cosmetic mask described herein on a subject's skin. In some embodiments, the methods may further include exposing the mask to light of a wavelength of about 630 nm to about 660 nm, light of a wavelength of about 420 nm to about 460 nm, or a combination of light sources of a wavelength of about 630 nm to about 660 nm and about 420 nm to about 460 nm.

Embodiments of the present disclosure may also provide adaptogenic action in a mask that encourages balance, epigenetic homeostasis and resistance in skin that is affected by stress, inflammation and imbalance.

The compositions, devices and related methods herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

DETAILED DESCRIPTION

Several aspects of the disclosure are described below. It should be understood that numerous specific details, relationships, and methods are set forth to provide a full understanding of the disclosure. One having ordinary skill in the relevant art, however, will readily recognize that the aspects of the disclosure can be practiced without one or more of the specific details or practiced with other methods, protocols, and animals. The present disclosure is not limited by the illustrated ordering of acts or events, as some acts may occur in different orders and/or concurrently with other acts or events. Furthermore, not all illustrated acts, steps or events are required to implement a methodology in accordance with the present disclosure. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a" and "an," and the definite article "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to an animal. Typically, the terms "subject" and "patient" may be used interchangeably herein in reference to a subject. As such, a "subject" includes a human that is being treated for a skin ailment, such as acne, or for anti-aging or skin rejuvenation.

The term "animal," includes, but is not limited to, dog, cat, pig, monkey, chimpanzee, and human.

The present disclosure provides compositions, devices and related methods of treatment for skin, such as for skin rejuvenation, acne treatment or anti-aging (e.g., wrinkle reduction). In one aspect, the present disclosure provides topical compositions for applying to skin, the compositions comprising a light activated enzymatic extract; Baobab seed extract; wild indigo (*Tephrosia purpurea*) extract; pre- and/or pro-biotic extracts; and a carrier.

The term "carrier" refers to a diluent, adjuvant, hydrocolloid, emulsifying agent, excipient, and/or vehicle with which the composition is administered. In preferred embodiments, the carrier is utilized as a topical gel or serum. Such pharmaceutical carriers can be sterile liquids, such as water and oils, including those of petroleum, animal, vegetable or synthetic origin, such as plant seed oils, nut oils, mineral oil, lanolin, esters, wax based ingredients, and the like. Suitable pharmaceutical excipients include starch, glucose, sucrose, gelatin, lactose, malt, rice, flour, chalk, silica gel, sodium stearate, glycerol monostearate, talc, sodium chloride, glycerol, propylene glycol, butylene glycol, propanediol, sorbitol, water, ethanol and the like. The composition(s) may also contain wetting or emulsifying agents or suspending/diluting agents, or pH buffering agents, or agents for modifying or maintaining the rate of release of the compositions, such as but not limited to, sodium acrylate, acryloyldimethyl taurate copolymer, isohexadecane, and polysorbates, carbomers, ceteareth-20 (non-ionic polyoxyethylene ether of higher saturated fatty alcohols (cetyl/stearyl alcohol), thickening alcohol cetearyl alcohol NF, and combinations thereof, at total concentrations of, for example, about 0.5 to 5% (v/v). The compositions can take the form of solutions, suspensions, emulsions, gels, creams, sustained-release compositions and the like. Compositions can include standard carriers such as pharmaceutical grades of mannitol, lactose, sodium saccharine, starch, magnesium stearate, cellulose, magnesium carbonate, etc. Such compositions will contain an effective amount of the components of the compositions together with a suitable amount of carrier so as to provide the proper form to the subject based on the mode of administration to be used. The compositions can also comprise one or more preservatives, astringents, humectants, and anti-oxidants, used either individually or in a mixture thereof. Antioxidants can include, but are not limited to, *Leontopodium alpinum* extract (bisabolane, sitosterol, tannin, chlorogenic acid, apigenin-7-glucoside, luteolin, luteolin-4-glucoside); Coenzyme Q10 (with vitamin E & C), (2,6-di-tert-butyl-4-methylphenol), any FDA-approved antioxidant widely used as stabilizer, citric acid, vitamin A (retinol palmitate), and combinations thereof. Preservatives can include, but are not limited to, tea tree essential oil (for example, at a concentration of 0.01 to 3.0%, w/w of the composition), rosemary leaf extract, phenylpropenes, cineole (eucalyptol), neem oil, propolis (produced by bees), rosemary extract, citric acid, alpha tocopherol (vitamin-E), potassium sorbate, sodium benzoate and combinations thereof.

The compositions can also comprise solid lipid emollient ingredients, such as USP petrolatum, solid lipid nanoparticles (SLN) or microparticles, nanostructured or microstructured lipid carriers, bees wax, jojoba gel, carnauba wax, octyldodecanol, triglyceride, and combinations thereof. As would be understood by those skilled in the art, nanoparticles include particles that are about 100 nm or less and microparticles include particles about 200 nm or greater in size.

In accordance with one implementation, the light activated enzymatic extract comprises an enzyme from a blue-green algae. The light activated enzymatic extract may include components such as photolyase, other planktonic enzymes, acai polyphenols (red light activated), wolfberry (goji) amino acids (red light activated), tara tree extract, seaweed extract, and combinations thereof.

In some embodiments, the enzyme is photolyase. Photolyase absorbs visible light to directly cleave and reverse damage caused by shorter wavelength UV. The photolyase may be derived from a photosynthetic plankton called *Anacystis nidulans*. In additional embodiments, the photolyase enzyme may be contained in multilamellar liposomes, which may be about 200 nanometers in size. The liposomes can be formed from pure soy phospholipids.

In some embodiments, the light activated enzymatic extract may be activated by light of wavelength in a range from about 420 nm to about 460 nm. This wavelength of light is visually in the blue spectrum. In other embodiments, the light activated enzymatic extract may be activated by light of wavelength in a range from about 630 nm to about 700 nm. This wavelength of light is visually in the red spectrum. In yet other embodiments, the light activated enzymatic extract may be activated by either light of wavelength from about 420 nm to about 460 nm or light of wavelength from about 630 nm to about 700 nm.

The compositions described in this disclosure can include pre/probiotics which can include alpha-glucooligosaccharides, plant juices rich in beta-fructooligosaccharides (from jicama or yacon tubers (*Polymnia sonchifolia*), and *Lactobacillus* probiotic bacteria (*L. casei, L. acidophilus*). The pre/probiotics act to stimulate and rebalance the beneficial microflora on the skin, increasing natural skin defenses. They also protect the skin from an overgrowth of acne causing bacteria.

In some embodiments, the composition described herein includes a Baobab seed extract. Such extracts may comprise plant ribonucleic acid molecules. Baobab seed extract is associated with adaptogenic effects including maintenance of the key enzymes essential for the maturation of skin microRNAs (e.g., Drosha and Dicer) to help improve epigenetic homeostasis and resistance. An increasing number of scientific studies are uncovering the biological activity of small RNAs on body health and wellbeing, in particular the small RNAs found in the food provided by the plants. These small RNAs have been described in plants as being a possible origin for rapid adaption to environmental stress for survival and longevity. The Baobab seed extract is, thus, rich in plant small RNAs to improve and maintain skin homeostasis while helping reduce the appearance of wrinkles and provide skin hydration. Baobab is also shown to increase collagen, elastin and HA synthesis and hydration.

In some embodiments, the composition described herein includes wild indigo (*Tephrosia purpurea*) extract, which may be from the seed of the plant. Wild indigo is a native Indian plant used in the Ayurvedic tradition for its adaptogenic effects on skin. A specific extraction from the seeds of this plant is utilized to obtain a condensate enriched in specific sugars, including stachyose and ciceritol. The wild indigo extract's adaptogenic effects include its ability to break down cortisol production by skin cells, its ability to activate the release of a natural calming neuropeptide acting on mood, and it improves skin tone. The extract also stimulates the production of beta-endorphin, a natural relaxing and pain-relief peptide, by skin cells and stimulates the expression of genes involved in the skin cells' homeostasis. Genes stimulated include, for example, hem oxygenase, the major cellular response to stress factors; NADPH quinone dehydrogenase 1 and heme oxygenase, involved in oxidative stress response; and genes involved in iron and heavy metal detoxification (Ferritin, metallothionein), antimicrobial markers (LL37 cathelicidin), skin barrier markers (ATP binding cassette transporter), anti-inflammatory markers (interleukin 1-alpha), and redox homeostasis markers (thioredoxin reductase).

The compositions provided in this disclosure can further include one or more of the following: willowherb extract (which is an anti-acne botanical that also soothes and reduces redness), colloidal sulfur (which is a gentle keratolytic with pore cleaning action), niacinamide (improves healthy skin tone and texture), a *Thermus thermophilus* extract, narnginen (an antioxidant), provitamin B5 (calms post-procedure redness), *arnica* extract (prevents bruising and trauma), one or more growth factors (such as, for example, TGF-beta), night blooming Chinese cucumber extract (*Trichosanthes kirilowii*), night blooming *cereus* cactus (moisturizes, softens and soothes skin), chamomile, lavender, and night blooming jasmine.

Night blooming Chinese cucumber extract (*Trichosanthes kirilowii*) (generally obtained from the root of the plant) protects skin against DNA damage induced by ultra-violet (UV) light, improves wrinkles in skin, and normalizes any disturbed circadian rhythm of the skin.

*Thermus thermophilus* is a micro-organism that thrives in deep sea thermal vents. Its extract is activated by heat and has the adaptogenic effects of preventing visible signs of photo-aging (spots, wrinkles, and dryness). It can counteract reactive oxygen species (ROS) production and promotes epidermal integrity and moisture maintenance post procedure. It would be understood that those skilled in the art that the present disclosure encompasses other micro-organismal extracts that are activated by heat.

In another aspect, the present disclosure provides a cosmetic mask for application to skin which contains the compositions described herein embedded in, disposed on, infused or integrated into, or impregnated into, or otherwise applied to a hydrogel or bio-cellulose or fibrous matrix or other suitable substrate. Such masks can be designed to cover the entire face, forehead and neck regions of a subject. In some implementations, a mask may cover the face, neck, shoulders, and décolleté of a subject, although smaller masks may be used for more targeted applications.

In a further aspect, the present disclosure provides a method of treating skin for acne or skin rejuvenation or preventing skin aging comprising placing the mask on a subject's skin. In particular, when treating for acne, the mask described herein can be exposed to blue wavelength light (about 420 nm to about 460 nm) upon application on the face. This kills unwanted surface acne causing bacteria, while also activating the light activated enzymes embedded in the mask.

"Treating" or "treatment" of any skin ailments refers, in one embodiment, to ameliorating the ailment (i.e., arresting or reducing the development of the ailment (i.e., acne) or at least one of the clinical symptoms thereof). In another embodiment, "treating" or "treatment" refers to ameliorating at least one physical parameter, which may not be discernible by the subject. In yet another embodiment, "treating" or "treatment" refers to modulating the ailment, either physically, (e.g., stabilization of a discernible symptom), physiologically, (e.g., stabilization of a physical parameter), or both. In yet another embodiment, "treating" or "treatment" refers to delaying the onset of the ailment (wrinkles (i.e., aging)). It would also be understood by a skilled artisan how to use the compositions and masks described herein for therapeutic purposes without undue experimentation based on the teachings provided throughout the specification.

"Preventing" or "prevention" refers to a reduction or slowing of skin aging symptoms (e.g., wrinkles).

It is also understood and contemplated that aspects of the present disclosure can provide more than two ingredient components in the compositions and masks herein disclosed. For example, a composition can comprise a light activated enzyme and/or any one or more component disclosed herein, such as, e.g., heat activated enzymes. Also, the disclosed methods can comprise the simultaneous or separate administration of multiple components by way of the masks described herein. Thus, the present disclosure may further include the administration of a mask having a third, fourth, etc. ingredient, wherein the third, fourth, etc. ingredient is administered separately (in a separate mask), but at substantially the same time as the other active ingredients, or hours or days after the first administration of ingredients (mask).

Further, the masks have unique and innovative photodynamic ingredients that activate their anti-aging powers upon exposure to either red or blue light (as described previously herein). Upon application of the mask, one can also expose the mask to light of a wavelength of about 630 nm to about 660 nm, a light of a wavelength of about 420 nm to about 460 nm, or a combination of light of a wavelength of about 630 nm to about 660 nm and about 420 nm to about 460 nm, to activate any light activated enzymatic extracts in the compositions embedded therein. The use of red wavelength light also stimulates anti-aging action within the skin. The use of such photodynamic therapies is further described in Juhasz et al., "The two faces of fractionated photodynamic therapy: Increasing efficacy with light fractionation or adjuvant use of fractional laser technology" *Journal of Drugs in Dermatology*, 15:11 (November 2016), which is incorporated herein in its entirety.

The masks described herein may be made of a natural hydrogel or bio-cellulose material, one of the most advanced and highest quality materials available. This unique material contains the compositions described within its matrix and is able to deliver the composition more efficiently and deeper into the skin (almost 200×) than results that can be achieved using the compositions alone (without a mask or fibrous/gel matrix or other material to which the composition may be applied). The masks' thin and pliable texture is like a 'second skin' and adheres to the skin effortlessly, with a cooling and soothing feel to it. Unlike other sheet masks, the composition embedded in the matrix makes it luxurious and easy to use, and not messy or wet like standard sheet masks. The masks are designed to treat the entire cosmetic area of the face, the neck, plus décolleté. This larger surface area and custom fit is a unique and defining factor compared to conventional applications.

It is to be appreciated that the foregoing Detailed Description section, and not the Abstract section, is intended to be used to interpret the claims. The Abstract section may set forth one or more, but not all, examples of the subject matter described in the present disclosure, and thus, is not intended to limit the present invention and the appended claims in any way.

The foregoing description of the specific embodiments should fully reveal the general nature of the disclosure so that others can, by applying knowledge within the skill of the art, readily modify and/or adapt for various applications such specific embodiments, without undue experimentation, without departing from the general concept of the present disclosure. Since many modifications, variations and changes in detail can be made to the described subject matter, it is intended that all matters in the foregoing description be interpreted as illustrative and not in a limiting sense. Thus, the scope of the invention should be determined by the appended claims and their legal equivalents. Moreover, the breadth and scope of the present disclosure should not be limited by any of the above-described examples, but should similarly be defined only in accordance with the following claims and their equivalents.

All patents, patent applications, provisional applications, and publications referred to or cited herein are incorporated by reference in their entirety, including all figures and tables, to the extent they are not inconsistent with the explicit teachings of this specification. By citation of various references in this document, Applicants do not admit any particular reference is "prior art" to their invention.

What is claimed is:

1. A topical composition or applying to skin, the composition comprising cosmetically effective amounts of:
    (i) an algal or plant extract comprising at least one light activated enzyme;
    (ii) Baobab (*Adansonia* sp.) seed extract;
    (iii) wild indigo (*Tephrosia purpurea*) extract;
    (iv) pro-biotic extracts; and
    (v) a carrier.

2. The composition of claim 1, wherein the alga that is extracted is a blue-green alga.

3. The composition of claim 2, wherein the enzyme is photolyase.

4. The composition of claim 2, wherein the blue-green alga is *Anacystis nidulans*.

5. The composition of claim 1, wherein the enzyme is activated by light of a wavelength from about 420 nm to about 460 nm.

6. The composition of claim 1, wherein the enzyme is activated by light of a wavelength from about 630 nm to about 700 nm.

7. The composition of claim 1, wherein the algal or plant extract comprises components selected from the group consisting of photolyase, planktonic enzymes, acai polyphenols, tara tree extract, seaweed extract, and combinations thereof.

8. The composition of claim 1, wherein the Baobab seed extract comprises plant ribonucleic acid molecules.

9. The composition of claim 1, wherein the wild indigo extract is from the seed of the plant.

10. The composition of claim 8, wherein the Baobab seed extract provides adaptogenic effects.

11. The composition of claim 9, wherein the wild indigo extract provides adaptogenic effects.

12. The composition of claim 1, wherein the composition is in a topical gel form.

13. The composition of claim 1, further comprising a bacterial extract comprising at least one heat activated enzyme.

14. The composition of claim 13, wherein the bacterium is *Thermus thermophiles*.

15. The composition of claim 1, further comprising night blooming jasmine.

* * * * *